United States Patent [19]

Janssen

[11] 4,210,646

[45] Jul. 1, 1980

[54] ANTIMICROBIAL COMPOSITIONS CONTAINING 1-(ARYLOXYPHENYL)PIPERAZINES

[75] Inventor: Marcel A. C. Janssen, Vosselaar, Belgium

[73] Assignee: Janssen Pharmaceutica, N.V., Beerse, Belgium

[21] Appl. No.: 895,166

[22] Filed: Apr. 11, 1978

[51] Int. Cl.² .......................... A01N 9/00; A01N 9/22
[52] U.S. Cl. .................................... 424/250; 544/392; 544/395
[58] Field of Search ................. 424/250; 544/392, 395

[56] References Cited

U.S. PATENT DOCUMENTS 4,064,245 12/1977 Beregi et al. ........................ 544/395

*Primary Examiner*—Allen J. Robinson
*Attorney, Agent, or Firm*—Salvatore R. Conte

[57] ABSTRACT

Novel antimicrobial compositions comprising a 1-(aryloxyphenyl)piperazine as an active ingredient and a method of combatting the growth of microorganisms by the use of such 1-(aryloxyphenyl)piperazines.

6 Claims, No Drawings

ANTIMICROBIAL COMPOSITIONS CONTAINING 1-(ARYLOXYPHENYL)PIPERAZINES

BACKGROUND OF THE INVENTION

A number of the 1-(aryloxyphenyl)piperazines with which the present invention is concerned and their preparation are described in Belg. Pat. No. 844,343, wherein it is pointed out that the concerned compounds exert a regulatory activity on the metabolism of lipids and carbohydrates and that, as a result, they can be used as pharmaceuticals, particularly in the prevention and treatment of such metabolic disorders as, for example, hyperlipidemy, obesity and arteriosclerosis. It has now unexpectedly been found that the subject compounds possess valuable antimicrobial, more particularly antifungal and antibacterial, properties.

DESCRIPTION OF THE PREFERRED EMBODIMENTS

The 1-(aryloxyphenyl)piperazines with which this invention is concerned are structurally represented by the formula

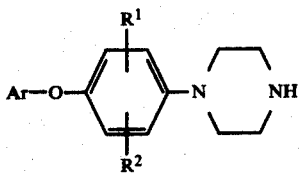

and the physiologically acceptable acid addition salts thereof, wherein:

$R^1$ and $R^2$ are each independently selected from the group consisting of hydrogen, halo, lower alkyl, lower alkyloxy, cyano, trifluoromethyl and lower alkyloxycarbonyl; and Ar is a member selected from the group consisting of phenyl, substituted phenyl, naphthalenyl, pyridinyl, thienyl, mono- and di-(lower alkyl)thienyl and furanyl, wherein said substituted phenyl is phenyl having from 1 to 3 substituents independently selected from the group consisting of halo, lower alkyl, lower alkyloxy, trifluoromethyl, cyano, hydroxy(lower alkyl), lower alkylcarbonyl, nitro, amino and mono- and di(lower alkyl)amino.

As used herein "lower alkyl" is meant to include straight and branch chained hydrocarbon radicals having from 1 to 6 carbon atoms, such as, for example, methyl, ethyl, 1-methylethyl, 1,1-dimethylethyl, propyl, butyl, pentyl, hexyl and the like, and the term "halo" is generic to fluoro, chloro, bromo and iodo.

The compounds of formula (I) can generally be prepared by the reaction of an appropriately substituted benzenamine of formula (II) wherein Ar, $R^1$ and $R^2$ are as previously defined, with 2-chloro-N-(2-chloroethyl)ethanamine, (III), or an acid addition salt thereof, e.g. the hydrochloride.

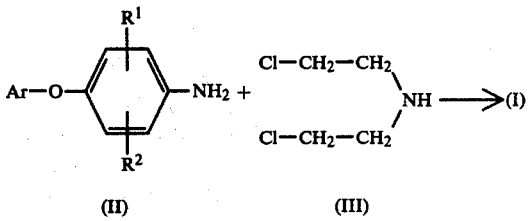

The reaction of (II) with (III) is conveniently carried out by stirring and heating, preferably refluxing, the reactants together in an appropriate reaction-inert organic solvent and in the presence of an appropriate base to pick up the acid which is liberated during the course of the reaction.

Suitable reaction-inert organic solvents which may be employed therefor include relatively polar solvents having a boiling point above 70° C., such as, for example, aliphatic alcohols, e.g. ethanol, 2-propanol, butanol, hexanol and the like; alkoxyalcohols, e.g. 2-butoxyethanol, 2-ethoxyethanol and the like. Appropriate bases include alkali metal carbonates and hydrogen carbonates, e.g. potassium or sodium carbonate. In order to enhance the reaction rate it may be advantageous to add to the reaction mixture an appropriate iodide salt, preferably an alkali metal iodide such as sodium or potassium iodide.

In view of their basic properties, the compounds of formula (I) can be converted to their physiologically acceptable acid addition salt form by the reaction with an appropriate acid, such as, for example, an inorganic acid such as hydrohalic acid, i.e., hydrochloric, hydrobromic or hydroiodic; sulfuric, nitric or thiocyanic acid; a phosphoric acid; an organic acid such as acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydrobutanedioic, 2-hydroxy-1,2,3-propanetricarboxylic, benzoic, 3-phenyl-2-propenoic, α-hydroxybenzeneacetic, methanesulfonic, ethanesulfonic, hydroxyethanesulfonic, 4-methylbenzenesulfonic, 2-hydroxybenzoic, 4-amino-2-hydroxybenzoic, 2-phenoxybenzoic, 2-acetyloxybenzoic, 2,4-hexanedienoic and 1,5-naphthalenedicarboxylic acid.

The compounds of formula (I) and their physiologically acceptable acid addition salts are found to possess valuable antimicrobial, particularly antifungal and antibacterial properties, and as a result they may be used as active ingredients in antifungal and antibacterial compositions.

The compounds of formula (I) are found especially useful against phytopathogenic fungi and consequently they may be used to protect crops from attack by such fungi as, for example, Phycomycetes, e.g. species of the genera Pythium, Phytophthora and Plasmopara; Basidiomycetes, e.g. species of the genera Ustilago, Puccinia and Uromyces; Ascomycetes, e.g. species of the genera Erysiphe, Podosphaera, Sphaerotheca, Uncinula, Venturia and Sclerotinia; and Fungi Imperfecti, e.g. species of the genera Septoria, Alternaria, Colletotrichum, Botrytis, Cercospora, Cladosporium, Fusarium, Thielaviopsis, Verticillium, Rizoctonia and Sclerotium.

The subject compounds are found especially active against Phytophthora species, in particular *Phytophthora infestans* causing late blight on potatoes, and against Botrytis species, such as *Botrytis cinerea*, causing gray mold and blight on many plants.

The compounds of formula (I) are also found active against bacteria such as, for example, *Salmonella pullorum gallinarum, Escherichia coli, Pseudomonas aeruginosa, Erysipelothrix insidiosa*, Staphylococcus sp. and Streptococcus sp.. In agriculture they can be used, for example, against bacteria of the genera Xanthomonas, Erwinia, Pseudomonas and Corynebacterium.

The useful antifungal and antibacterial properties of the compounds of formula (I) are demonstrated in the following test procedures.

The compounds listed therein are not given for the purpose of limiting the invention thereto but in order to exemplify the useful antifungal properties of all the compounds within the scope of formula (I).

A. Activity against *Phytophthora infestans* on tomato plants

Young tomato plants, 6 to 8 cm high, individually potted in plastic pots of 8 cm diameter are sprayed until run-off with an aqueous formulation of the test compound, prepared by first formulating 100 mg of the compound in 4 ml acetone+2 ml 0.5% Tween 20 and thereafter diluting with tap water until the desired concentration (100, 50 or 25 ppm) is reached. Control plants are treated in the same manner with solvent. After drying, the plants are artificially infected by spraying them with a suspension of sporangia of *P. infestans* and subsequently incubating the plants for 24 hours at 21°±1° C. and at 100% relative humidity. The plants are kept in the greenhouse for 2 to 4 days. Fungicidal activity is evaluated by estimating the percentage of the leaf surface attacked by the fungus. The results given in the following table I are mean values for 2 plants.

TABLE I

| | Compounds of formula I | | | Activity against *P. infestans* % attack at stated dose | | |
|---|---|---|---|---|---|---|
| Compound No. | Ar | $R^1, R^2$ | Salt form | 100 ppm | 50 ppm | 25 ppm |
| 1 | 4-Cl—$C_6H_4$ | H | HCl | 3 | 7 | 17 |
| 2 | 4-Cl—$C_6H_4$ | 3-Cl | HCl | 1 | 1 | 5 |

B. Activity against *Botrytis cinerea* on broad beans (*Vicia faba*)

About 15 cm high bean plants are sprayed until run-off with an aqueous formulation of the test compound, prepared by first formulating 100 mg of the compound in 4 ml acetone+2 ml 0.5% Tween 20 and thereafter diluting with tap water until the desired concentration (100, 50 or 25 ppm) is reached.

After drying, the plants are artificially infected by spraying them with a suspension of spores of *B. cinerea*. The plants are kept in an incubator for 48 hours at 21°±1° C. and at 100% relative humidity.

Fungicidal activity of the compounds is evaluated by estimating the % attack as compared to the untreated infected control plants. The results given in the following table II are mean values for 2 plants.

TABLE II

| Compounds of formula I | | | Activity against *B. Cinerea* % attack at stated dose | | |
|---|---|---|---|---|---|
| Ar | $R^1R^2$ | Salt form | 100 ppm | 50 ppm | 25 ppm |
| 4-Cl—$C_6H_4$ | 3-CN | HCl | 2.5 | 2 | 3 |
| 2-$CH_3$-4-($tC_4H_9$)—$C_6H_3$ | 3-($CF_3$) | HCl | 1 | 0.5 | 0.5 |
| 3-Cl—$C_6H_4$ | 3-Cl | HCl | 0.5 | 10 | 18 |
| 3,4-$Cl_2$—$C_6H_3$ | 3-Cl | HCl | 1.5 | 1 | 15 |
| 3,4-$Cl_2$—$C_6H_3$ | 3-($CF_3$) | HCl | 1 | 1 | 1.5 |

C. Antibacterial activity

Antibacterial tests were performed on cultures on phenol red dextrose broth medium (Difco) in test tubes, each containing 4.5 ml of liquid medium, autoclaved at 120° C. for 15 min. The test solutions were prepared by dissolving the test compound in 50% ethanol to a concentration of 20 mg/ml and thereafter diluting with sterile distilled water to obtain a concentration of 10 mg/ml. Successive decimal dilutions were then made with sterile distilled water to prepare a series of test solutions. In carrying out the test, 0.5 ml of one of the test solutions is added to 4.5 ml of phenol red dextrose broth medium to obtain a test medium. Test media containing 100 µg, 10 µg and 1 µg of the test compound per milliliter of medium were obtained. Control media were prepared by adding 0.5 ml of sterile distilled water to 4.5 ml of medium. Table III shows results with representative compounds which demonstrate both broad activity and high activity toward representative gram-positive and gram-negative bacteria.

The following abbreviations are used to indicate the bacterial species tested:

Sp. G=*Salmonella pullorum gallinarum*
E. Coli=*Escherichia coli*
Ps. Aer.=*Pseudomonas aeruginosa*
E. Ins.=*Erysipelothrix insidiosa*
Staph.=*Staphylococcus hemolyticus*
Strep.=*Streptococcus pyogenes.*

TABLE III

| Compound No. | Concentration in µg/ml for 100% growth inhibition Organism: | | | | | |
|---|---|---|---|---|---|---|
| | Sp. G. | E. Coli | Ps Aer. | E. ins. | Staph. | Strep. |
| 1 | 100 | 100 | 100 | 100 | 100 | 100 |
| 2 | 100 | 100 | >100 | 100 | 100 | 100 |

In view of the aforementioned antifungal and antibacterial activities, this invention provides valuable compositions comprising compounds of formula (I) and addition salts thereof as the active ingredient in a solvent or a solid, semi-solid or liquid diluent or carrier. In addition it provides an effective method of combatting fungi and bacteria by use of an effective antifungal or antibacterial amount of a compound of formula (I) or an acid addition salt thereof. The compounds of formula (I) are essentially non-toxic to plants and in view of their excellent activity against phytopathogenic fungi and bacteria they are especially useful for the protection of crops, individual plants and parts of plants, including growing and harvested fruits, blossom, foliage, stems, tubers, roots, seed, etc... The subject compounds can however also be used in other circumstances e.g. as preservatives and desinfectants, for example, to preserve organic materials such as wood, plastics, paints, jute, photographic emulsions etc., and as desinfectants, e.g. in soaps, detergents, cooling water, oils etc..

The subject compounds can be used in suitable solvents or diluents, in the form of emulsions, suspensions, dispersions or ointments, on suitable solid or semi-solid carrier substances, in ordinary or synthetic soaps, detergents or dispersion media, if desired, together with other compounds having arachnicidal, insecticidal, ovicidal, fungicidal and/or bactericidal effects, or together with inactive additives.

Solid carrier substances which are suitable for the preparation of compositions in powder form include various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr clay and boric acid; powdered cork, sawdust, and other fine pulverous materials of vegetable origin are also suitable carrier substances.

The compound of formula (I) or salt thereof is mixed with these carrier substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, pulverous preparations can also be made readily wettable with water, so that suspensions are obtained.

Inert solvents used for the production of liquid preparations should preferably not be readily inflammable and as far as possible non-toxic to warm-blooded animals or plants in the relevant surroundings. Solvents suitable for this purpose are high-boiling oils, for example, of vegetable origin, and lower-boiling solvents, such as, for example, isopropanol, dimethylsulfoxide, hydrogenated naphthalenes, alkylated naphthalenes, alkoxyalkanols, etc.. It is of course, also possible to use mixtures of solvents. Solutions can be prepared in the usual way, if necessary, with assistance of solution promoters. Other liquid forms which can be used consist of emulsions or suspensions of the active compound in water or suitable inert solvents, or also concentrates for preparing such emulsions, which can be directly adjusted to the required concentration. For this purpose, the compound of formula (I) or salt thereof is, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the compound of formula (I) or salt thereof can be incorporated, if necessary, with the aid of solution promoters and/or emulsifiers. Vaseline and other cream bases are examples of semi-solid carrier substances.

Furthermore, it is possible for the subject compounds to be used in the form of aerosols. For this purpose, the active component is dissolved or dispersed, if necessary with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combatting fungi and bacteria; e.g. in closed chambers and storage rooms, and for application to vegetation for eradicating or for preventing infection by fungi or bacteria.

The compounds of formula (I) and salts thereof, and compositions thereof can be applied by conventional methods. For example, a fungus or bacterial growth or a material to be treated or to be protected against attack by fungus or bacterium can be treated with the subject compounds and the compositions thereof by dusting, sprinkling, spraying, brushing, dipping, smearing, impregnating or other suitable means.

When the compounds are employed in combination with suitable carriers, e.g., in solution, suspension, dust, powder, ointment, emulsion and the like forms, a high activity over a very high range of dilution is observed. Effective antifungal or antibacterial compositions according to the present invention may contain from about 0.001 to about 15% and preferably from about 0.01 to about 10% of the active ingredient. Of course, higher concentrations may also be employed as warranted by the particular situation. Commercial preparations can contain from about 0.1 to about 90% and preferably from about 1 to about 80% of the active ingredient.

Preferred commercial preparations are concentrated forms, containing from about 5 to about 90% and preferably from about 10 to about 70% of the active ingredient.

The following examples are intended to illustrate but not to limit the scope of the invention. Unless otherwise stated all parts are by weight.

EXAMPLE I

A mixture of 9 parts of 2-chloro-N-(2-chloroethyl)ethanamine hydrochlorine, 12.7 parts of 3-chloro-4-(4-chlorophenoxy)-benzenamine and 28 parts n-butanol is stirred and refluxed for 24 hours. The mixture is cooled and 3.5 parts of potassium carbonate are added. Stirring is continued for another 24 hours at reflux. The reaction mixture is filtered hot and the product is crystallized after cooling the filtrate. 2,2'-Oxybispropane is added and the precipitated product is filtered off. It is crystallized from a mixture of 2-propanol and 2,2'-oxybispropane, yielding 10.5 parts of 1-[3-chloro-4-(4-chlorophenoxy)phenyl]piperazine hydrochloride; mp. 187.7° C.

EXAMPLE II

Following the procedure of Example I and using equivalent amounts of the appropriate starting materials the following compounds are still prepared:

| Ar | $R^1, R^2$ | Base or Salt form | Melting point °C. |
|---|---|---|---|
| 2,4-$Cl_2$—$C_6H_3$ | 3-Cl | HCl | 218 |
| 4-Cl—$C_6H_4$ | H | HCl | 250 |
| 2-($CH_3$)-4-Cl—$C_6H_3$ | 3-Cl | HCl | 223.4 |
| 2,4-$Cl_2$—$C_6H_3$ | H | HCl | 177.5 |
| 2,4-$Cl_2$—$C_6H_3$ | 3-(CN) | HCl | 261.7 |
| 4-Cl—$C_6H_4$ | 3-(CN) | HCl | 260.3 |
| 2,4-$Cl_2$—$C_6H_3$ | 3-($CF_3$) | HCl | 263–268 |
| 4-Cl—$C_6H_4$ | 3-($CF_3$) | HCl | 218.8 |
| 2-($CH_3$)-4-(t.$C_4H_9$)—$C_6H_3$ | 3-($CF_3$) | HCl | 284.2(dec.) |
| 3-Cl—$C_6H_4$ | 3-Cl | HCl | 237.6 |
| 3,4-$Cl_2$—$C_6H_3$ | 3-Cl | HCl | 216.2(dec.) |
| 2,4,6-$Cl_3$—$C_6H_2$ | 3-($CF_3$) | HCl | 262–285(dec.) |
| 3,4-$Cl_2$—$C_6H_3$ | 3-($CF_3$) | HCl | 220.2(dec.) |
| 2,4,5-$Cl_3$—$C_6H_2$ | 3-($CF_3$) | base | 135.5–136.5 |
| 4-Br—$C_6H_4$ | 3-($CF_3$) | HCl | 227–228 |

-continued

| Ar | R¹, R² | Base or Salt form | Melting point °C. |
|---|---|---|---|
| 3-Cl—C₆H₄ | 3-(CF₃) | HCl | 217–229 (dec.) |
| 3-(CF₃)-4-Cl—C₆H₃ | 3-(CF₃) | HCl | 264.2 (dec.) |
| 4-Cl—C₆H₄ | 3-(COOCH₃) | HCl | 207 (dec.) |
| 2-(CN)—C₆H₄ | 3-Cl | HCl | 247.5 (dec.) |
| 3,4-Cl₂—C₆H₃ | 3-(COOCH₃) | HCl | 220 |

What is claimed is:

1. An antifungal and antibacterial composition comprising an inert carrier material and as an active ingredient an effective amount of a compound selected from the group consisting of 2-(4-chlorophenoxy)-5-(1-piperazinyl)benzonitrile and the physiologically acceptable acid addition salts thereof.

2. An antifungal and antibacterial composition comprising an inert carrier material and as an active ingredient an effective antifungal and antibacterial amount of a compound selected from the group consisting of 1-{4-[4-(1,1-dimethylethyl)-2-methylphenoxy]-3-(trifluoromethyl)-phenyl}piperazine and the physiologically acceptable acid addition salts thereof.

3. An antifungal and antibacterial composition comprising an inert carrier material and as an active ingredient an effective antifungal and antibacterial amount of a compound selected from the group consisting of 1-[3-chloro-4(3,4-dichlorophenoxy)phenyl]piperazine and the physiologically acceptable acid addition salts thereof.

4. An antifungal and antibacterial composition comprising an inert carrier material and as an active ingredient an effective antifungal and antibacterial amount of a compound selected from the group consisting of 1-[4-(3,4-dichlorophenoxy)-3-(trifluoromethyl)phenyl]-piperazine and the physiologically acceptable acid addition salts thereof.

5. An antifungal and antibacterial composition comprising an inert carrier material and as an active ingredient an effective antifungal and antibacterial amount of a compound selected from the group consisting of 2-(2,4-dichlorophenoxy)-5-(1-piperazinyl)benzonitrile and the physiologically acceptable acid addition salts thereof.

6. A method of combatting the growth of microorganisms selected from the group consisting of fungi and bacteria which comprises contacting said microorganisms with an effective antifungal and antibacterial amount of a compound selected from the group consisting of a 1-(aryloxyphenyl)piperazine having the formula

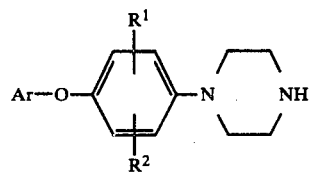

and the physiologically acceptable acid addition salts thereof, wherein:

R¹ and R² are each independently selected from the group consisting of hydrogen, halo, lower alkyl, lower alkyloxy, cyano, trifluoromethyl and lower alkyloxycarbonyl; and Ar is a member selected from the group consisting of phenyl, substituted phenyl and naphthalenyl, wherein said substituted phenyl is phenyl having from 1 to 3 substituents independently selected from the group consisting of halo, lower alkyl, lower alkyloxy, trifluoromethyl, cyano, hydroxy(lower alkyl), lower alkylcarbonyl, nitro, amino and mono- and di(lower alkyl)amino.

* * * * *

UNITED STATES PATENT AND TRADEMARK OFFICE
CERTIFICATE OF CORRECTION

PATENT NO. : 4,210,646
DATED : July 1, 1980
INVENTOR(S) : Marcel A.C. Janssen

It is certified that error appears in the above-identified patent and that said Letters Patent are hereby corrected as shown below:

At Column 7, Line 17, Claim 1: "effective amount" should be -- effective antifungal and antibacterial amount --.

Signed and Sealed this

Twentieth Day of January 1981

[SEAL]

Attest:

RENE D. TEGTMEYER

Attesting Officer

Acting Commissioner of Patents and Trademarks